(12) United States Patent
Teoh et al.

(10) Patent No.: US 8,702,808 B2
(45) Date of Patent: Apr. 22, 2014

(54) RESORBABLE SCAFFOLDS FOR BONE REPAIR AND LONG BONE TISSUE ENGINEERING

(75) Inventors: Swee Hin Teoh, Singapore (SG); Hae-Ryong Song, Seoul (KR); Soi Khoon Yew, Singapore (SG); Kelvin Hong Yap Koh, Singapore (SG); Ji Hoon Bae, Seoul (KR); Joon Ho Wang, Seoul (KR)

(73) Assignees: Osteopore International PTE Ltd, Singapore (SG); Osteopore Korea Co. Ltd, Seoul (KR); National University of Singapore, Singapore (SG)

( * ) Notice: Subject to any disclaimer, the term of this patent is extended or adjusted under 35 U.S.C. 154(b) by 155 days.

(21) Appl. No.: 13/124,161

(22) PCT Filed: Oct. 19, 2009

(86) PCT No.: PCT/SG2009/000384
§ 371 (c)(1),
(2), (4) Date: Jul. 29, 2011

(87) PCT Pub. No.: WO2010/044758
PCT Pub. Date: Apr. 22, 2010

(65) Prior Publication Data
US 2011/0307073 A1    Dec. 15, 2011

Related U.S. Application Data

(60) Provisional application No. 61/106,347, filed on Oct. 17, 2008.

(51) Int. Cl.
*A61F 2/28*   (2006.01)
(52) U.S. Cl.
USPC ....................................................... 623/23.61

(58) Field of Classification Search
USPC .......... 623/17.19, 16.11, 17.16, 18.11, 23.61, 623/23.72–23.76, 23.63; 606/151; 424/423
See application file for complete search history.

(56) References Cited

U.S. PATENT DOCUMENTS

| 5,124,195 A | 6/1992 | Harpell et al. |
| 5,294,395 A | 3/1994 | Broyer |

(Continued)

FOREIGN PATENT DOCUMENTS

| DE | 10 2005 018 644 A1 | 11/2005 |
| EP | 1 466 633 A1 | 10/2004 |

(Continued)

OTHER PUBLICATIONS

Notification Concerning Transmittal of International Preliminary Report on Patentability (IPRP) with IPRP, PCT/SG2009/000384, mailed Apr. 28, 2011.

(Continued)

*Primary Examiner* — Alvin J. Stewart
(74) *Attorney, Agent, or Firm* — Hamilton, Brook, Smith & Reynolds, P.C.

(57) ABSTRACT

Bioresorbable scaffolds for bone engineering, such as repair of bone defects, particularly long bone defects, or augmentation of bone length are described. Scaffolds are porous and comprise multiple side channels. In one embodiment, scaffolds are made from layers of micro-filament meshes comprising polycaprolactone (PCL) or a PCL-composite sequentially laid in incremental 60 degrees of rotation to produce a 0/60/120 degree layering pattern, providing for the formation of interconnected pores. The scaffold can comprise a central channel filled, packed or infused with suitable agents such as bioactive agents. Furthermore, the scaffolds are stiff but yet fracture resistant and with sufficient bending, compressive and torsional strength suitable for bone engineering. The slow degradation of the scaffold is sufficient for the 3D matrix to maintain structure integrity and mechanical properties during the remodelling process.

20 Claims, 11 Drawing Sheets

(56) References Cited

U.S. PATENT DOCUMENTS

| | | | |
|---|---|---|---|
| 5,518,680 A | | 5/1996 | Cima et al. |
| 5,549,679 A | | 8/1996 | Kuslich |
| 5,628,788 A | * | 5/1997 | Pinchuk ................... 623/1.2 |
| 5,716,408 A | * | 2/1998 | Eldridge et al. ............ 606/213 |
| 5,936,861 A | | 8/1999 | Jang et al. |
| 5,990,378 A | * | 11/1999 | Ellis ...................... 623/11.11 |
| 6,033,438 A | * | 3/2000 | Bianchi et al. ............ 623/17.16 |
| 6,129,872 A | | 10/2000 | Jang et al. |
| 6,174,320 B1 | * | 1/2001 | Kugel et al. ................ 606/151 |
| 6,187,329 B1 | * | 2/2001 | Agrawal et al. ............. 424/426 |
| 6,280,478 B1 | | 8/2001 | Richter et al. |
| 6,398,811 B1 | * | 6/2002 | McKay .................. 623/17.16 |
| 6,626,945 B2 | * | 9/2003 | Simon et al. ............. 623/17.19 |
| 6,632,246 B1 | * | 10/2003 | Simon et al. ............. 623/14.12 |
| 6,730,252 B1 | | 5/2004 | Teoh et al. |
| 6,916,321 B2 | * | 7/2005 | TenHuisen et al. ........... 606/312 |
| 7,141,066 B2 | * | 11/2006 | Steiner et al. ............. 623/13.12 |
| 7,300,439 B2 | * | 11/2007 | May ........................ 606/326 |
| 7,347,872 B2 | * | 3/2008 | Goulet et al. ............. 623/13.17 |
| 7,572,291 B2 | * | 8/2009 | Gil et al. ................. 623/14.12 |
| 7,632,311 B2 | * | 12/2009 | Seedhom et al. .......... 623/16.11 |
| 7,662,185 B2 | * | 2/2010 | Alfaro et al. ............. 623/17.16 |
| 7,803,574 B2 | * | 9/2010 | Desai et al. ................. 435/41 |
| 7,968,026 B1 | | 6/2011 | Teoh et al. |
| 7,972,616 B2 | * | 7/2011 | Dubrow et al. ............. 424/423 |
| 8,071,007 B1 | | 12/2011 | Teoh et al. |
| 2003/0009235 A1 | * | 1/2003 | Manrique et al. .......... 623/23.63 |
| 2003/0065332 A1 | * | 4/2003 | TenHuisen et al. ............ 606/73 |
| 2003/0090034 A1 | | 5/2003 | Mulhaupt et al. |
| 2004/0073309 A1 | * | 4/2004 | Bianchi et al. ............. 623/17.11 |
| 2005/0015088 A1 | * | 1/2005 | Ringeisen ................... 606/69 |
| 2005/0159812 A1 | * | 7/2005 | Dinger et al. ............. 623/13.14 |
| 2005/0183728 A1 | * | 8/2005 | Hunter et al. ............. 128/207.14 |
| 2005/0209705 A1 | * | 9/2005 | Niederauer et al. ........ 623/23.63 |
| 2005/0221072 A1 | * | 10/2005 | Dubrow et al. ............ 428/292.1 |
| 2006/0178748 A1 | * | 8/2006 | Dinger et al. ............. 623/18.11 |
| 2006/0204738 A1 | * | 9/2006 | Dubrow et al. ............ 428/292.1 |
| 2006/0282103 A1 | * | 12/2006 | Fricke et al. ................ 606/151 |
| 2007/0083268 A1 | * | 4/2007 | Teoh et al. ................ 623/17.19 |
| 2007/0185585 A1 | * | 8/2007 | Bracy et al. .............. 623/23.63 |
| 2007/0254035 A1 | * | 11/2007 | Hao et al. .................. 424/486 |
| 2008/0008737 A1 | * | 1/2008 | Harlow et al. ................ 424/423 |
| 2008/0077251 A1 | * | 3/2008 | Chen et al. ................ 623/23.72 |
| 2008/0095818 A1 | * | 4/2008 | Abatangelo et al. .......... 424/423 |
| 2008/0112998 A1 | * | 5/2008 | Wang ........................ 424/423 |
| 2009/0024229 A1 | * | 1/2009 | Chen et al. ................. 623/23.73 |
| 2010/0137990 A1 | * | 6/2010 | Apatsidis et al. .......... 623/17.16 |
| 2010/0190254 A1 | | 7/2010 | Chian et al. ................. 435/396 |
| 2010/0256777 A1 | * | 10/2010 | Datta et al. ............... 623/23.72 |
| 2011/0091515 A1 | * | 4/2011 | Zilberman et al. ............ 424/409 |
| 2011/0144764 A1 | * | 6/2011 | Bagga et al. .............. 623/23.61 |
| 2011/0307073 A1 | * | 12/2011 | Teoh et al. ............... 623/23.61 |
| 2012/0040581 A1 | * | 2/2012 | Kim ......................... 442/330 |
| 2012/0077010 A1 | * | 3/2012 | Manesis et al. ............. 428/220 |

FOREIGN PATENT DOCUMENTS

| | | |
|---|---|---|
| EP | 1 410 810 B1 | 1/2007 |
| EP | 0 895 762 B1 | 2/2008 |
| WO | WO 2005/048885 A1 | 6/2005 |
| WO | WO 2010/044758 A1 | 4/2010 |

OTHER PUBLICATIONS

Supplemental Amendment, U.S. Appl. No. 10/828,477, filed Apr. 21, 2011.
Notice of Allowance, U.S. Appl. No. 10/828,477, dated Apr. 27, 2011.
Huang, M.D., Q., et al., "In Vivo Mesenchymal Cell Recruitment by a Scaffold Loaded with Transforming Growth Factor β1 and the Potential for in Situ Chondrogenesis," *Tissue Engineering*, (3):469-482, (2002).
International Search Report from counterpart International Application No. PCT/SG2009/000384, dated Dec. 17, 2009.
Notification of Transmittal of the International Search Report (ISR) and the Written Opinion (WO) of the International Searching Authority, or the Declaration with copies of the ISR and WO, PCT/SG2009/000384, mailed Dec. 17, 2009.
Hutmacher, D.W., et al., "Design and Fabrication of a 3D Scaffold for Tissue Engineering Bone," as published in Agrawal et al., Eds. *Synthetic Bioadsorbable Polymers for Implants*. ASTM, West Conchohocken, PA, pp. 152-167 (2000).
Bandyopadhyay, et al., "Processing of Piezocomposites by Fused Deposition Technique," J. of the American Ceramic Society 80(6): 1366-1372 (1997).
Zein, et al., "Fused Deposition Modeling of Novel Scaffold Architectures for Tissue Engineering Applications," Biomaterials 23:1169-1185 (2002).
Office Action, U.S. Appl. No. 10/828,477, dated Jan. 9, 2007.
Office Action, U.S. Appl. No. 10/828,477, dated Oct. 16, 2007.
Office Action, U.S. Appl. No. 10/828,477, dated Jul. 10, 2008.
Office Action, U.S. Appl. No. 10/828,477, dated Apr. 29, 2009.
Office Action, U.S. Appl. No. 10/828,477, dated Nov. 12, 2009.
Office Action, U.S. Appl. No. 10/828,467, dated Feb. 4, 2011.
Office Action, U.S. Appl. No. 10/828,467, dated Apr. 29, 2010.
Office Action, U.S. Appl. No. 10/828,467, dated Jun. 23, 2005.
Final Office Action, U.S. Appl. No. 10/828,467, dated Dec. 20, 2005.
Office Action, U.S. Appl. No. 10/828,467, dated May 25, 2006.
Final Office Action, U.S. Appl. No. 10/828,467, dated Jan. 18, 2007.
Office Action, U.S. Appl. No. 10/828,467, dated May 25, 2007.
Final Office Action, U.S. Appl. No. 10/828,467, dated Nov. 16, 2007.
Office Action, U.S. Appl. No. 10/828,467, dated Jul. 28, 2008.
Final Office Action, U.S. Appl. No. 10/828,467, dated Apr. 17, 2009.
Office Action, U.S. Appl. No. 10/828,467, dated Oct. 7, 2009.
U.S. Appl. No. 10/828,477, filed Apr. 20, 2004.
U.S. Appl. No. 10/828,467, filed Apr. 20, 2004.
Notice of Allowance, U.S. Appl. No. 10/828,467, dated Aug. 5, 2011.

* cited by examiner

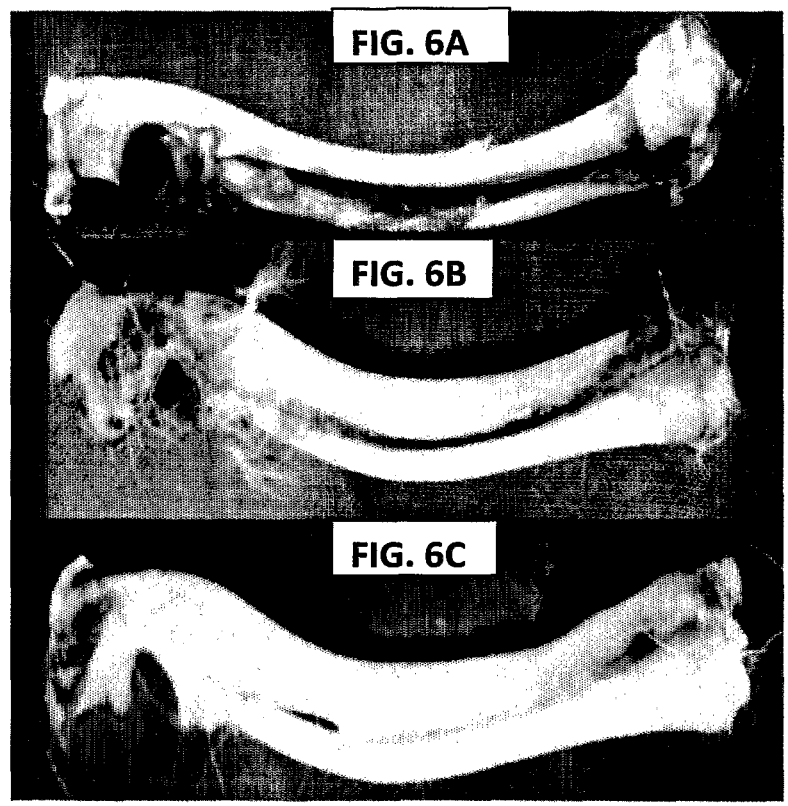

RESORBABLE SCAFFOLDS FOR BONE REPAIR AND LONG BONE TISSUE ENGINEERING

RELATED APPLICATIONS

This application is the U.S. National Stage of International Application No. PCT/SG2009/000384, filed Oct. 19, 2009, which designates the U.S., published in English, and claims the benefit of U.S. Provisional Application No. 61/106,347, filed Oct. 17, 2008. The entire teachings of the above application are incorporated herein by reference.

BACKGROUND OF THE INVENTION

Bone repair and reconstruction is an important clinical problem. It is estimated in United States alone, the number of bone repair procedures is more than 800,000 per year. The traditional biological methods include autografting and allografting of cancellous bone (also known as trabecular bone or spongy bone), applying vascularized grafts of the fibula and iliac crest, and using other bone transport techniques.

Today, bone grafting is increasing and the failure rate is high. In patients who receive various bone grafts, a failure rate ranging from 16% to 50% is reported. The failure rate of autografts is at the lower end of this range, but the need for a second (i.e., donor) site of surgery, limited supply, inadequate size and shape, and the morbidity associated with the donor site are all major issues. Furthermore, the new bone volume maintenance can be problematic due to unpredictable bone resorption. In large defects, the body can resorb the grafts before osteogenesis is complete.

The operating time required for harvesting autografts is expensive and often the donor tissue is scarce. There can be significant donor site morbidity associated with infection, pain, and hematoma. Allografting introduces the risk of disease and/or infection; it may cause a lessening or complete loss of the bone inductive factors. Vascularized grafts require a major microsurgical operative procedure requiring a sophisticated infrastructure. Distraction osteogenesis techniques are often laborious and lengthy processes that are reserved for the most motivated patients.

Tissue engineering osseous tissue by using cells in combination with a synthetic extracellular matrix is a new approach compared to the transplantation of harvested tissues. Numerous tissue-engineering concepts have been proposed to address the need for new bone graft substitutes. One potentially successful repair solution seeks to mimic the success of autografts by removing cells from the patient by biopsy and then growing sufficient quantities of mineralized tissue in vitro on implantable, 3D scaffolds for use as functionally equivalent autogenous bone tissue. In this way, reproducing the intrinsic properties of autogenous bone material creates an ideal bony regeneration environment, which includes the following characteristics: (i) a highly porous, 3D architecture allowing osteoblast, osteoprogenitor cell migration and graft revascularization; (ii) the ability to be incorporated into the surrounding host bone and to continue the normal bone remodeling processes; and (iii) the delivery of bone-forming cells and osteogenic growth factors to accelerate healing and differentiation of local osteoprogenitor cells.

Naturally-derived or synthetic materials are fashioned into scaffolds that, when implanted in the body as temporary structures, provide a template that allows the body's own cells to grow and form new tissues while the scaffold is gradually absorbed. Conventional two-dimensional scaffolds are satisfactory for multiplying cells, but are less satisfactory when it comes to generating functional tissues. For that reason, a three-dimensional (3D) bioresorbable scaffold system is preferred for the generation and maintenance of highly differentiated tissues. Ideally, the scaffold should have the following characteristics: (i) be highly porous with an interconnected pore network for cell growth and flow transport of nutrients and metabolic waste; (ii) be biocompatible and bioresorbable, with controllable degradation and resorption rates so as to substantially match tissue replacement; (iii) have suitable surface chemistry for cell attachment, proliferation and differentiation; (iv) have enough channels to promote vascular integration and (v) have mechanical properties to match those of the tissues at the site of implantation. In vivo, the scaffold structure should protect the inside of the pore network proliferating cells and their extracellular matrix from being mechanically overloaded for a sufficient period of time. This is particularly important for load-bearing tissues such as bone and cartilage. A biomechanically stable scaffold with mechano-induction properties is therefore sought after.

Porosity and pore sizes play a critical role in bone formation in vivo situations. Higher porosity and pore size has shown to result in greater bone ingrowth however the mechanical properties are diminished in such instances. Present limitations thus set an upper function limit for pore size and porosity. Repair of bone tissue, rate of remodeling is thus compromised.

The repair and reconstruction of large bone defects such as in the lengthening of the lower limb, has been a clinical challenge as such. This problem has yet to be solved. Presently none of the approaches proposed thus far have shown long term efficacy that resembles the natural bone. The era of tissue engineering involving stems cells and a suitable scaffold could provide the answer. However, a suitable scaffold has yet to be designed. Ceramics scaffolds such as macro porous hydroxyapatite (HA) (R. Quarto et al, 2001) have been tried with some clinical success. But ceramics are brittle material and the scaffolds are prone to premature fracture. In many cases HA ceramics are crystalline in nature and hence do not render it resorbable even after 6 years. Bioresorbable polymeric scaffolds have been used but none has been designed for long bone tissue applications. Those polymers with high glass transition temperature such as PGA and PLA are also brittle and some degrade too fast, hence are unable to evoke the long term mechano-induction required for proper bone remodeling process. The large volume of acid formation, as a by product of degradation, of those with too short a degradation time, also hinders the proper cell formation and growth of the bone. The other issue is that large scaffolds of this nature do not have enough channels to provide the rich vasculature of blood vessels for drainage of waste products as well as delivery of nutrients over the entire volume. Scaffolds with high porosity also do not have enough mechanical stability to be used for structural bone tissue engineering of the long bones.

SUMMARY OF THE INVENTION

The present invention describes a method of fabrication and the design of a porous (having interconnected pores) tubular scaffold that has a central channel and multiple side channels that is stiff but yet fracture resistant and with sufficient bending, compressive and torsional strength. The design which has a central channel to allow the packing or infusion of agents, such as cells, tissues, cell- or tissue-derived agents, growth factors, drugs and combinations thereof and side channels along the circumference of the scaffold structure to allow the communication of blood vessels. In one embodiment, the scaffold structure is made up of two portions (e.g., regions, or layers) comprising, consisting essentially of, or consisting of: an inner porous portion having a central channel with micro-channels along the plane surface, which provide, e.g., the primary site for osteogenesis and also provide compressive strength; and an outer porous portion wrapped around the inner portion, the outer portion having micro-channels along the axis (e.g., parallel, perpendicular, or a combination thereof, to the axis) of the central column, which provide for, e.g., cell proliferation, vascular integration as well as torsional and bending strength.

In one embodiment, the inner portion and the outer portion of the scaffold implant are manufactured separately by extrusion layer by layer of porous bioresorbable polymer or polymer composite. In one embodiment, a porous bioresorbable polymer or polymer composite is polycaprolactone (PCL) or PCL-ceramic composite mesh. A scaffold with fixed pattern designs is prepared. The scaffold is made from layers of micro-filament meshes. The micro-filaments in the meshes are in a parallel, or essentially parallel formation. Furthermore, the micro-filaments are spaced apart, such that the farther apart the micro-filaments are, the larger the pores in the scaffold will be formed, and vice versa, the closer the micro-filaments are spaced, the smaller the scaffold pores will be. Each micro-filament mesh is laid in layers, one on top of the other, such that each layer is laid with the micro-filaments at a different angle from the previous layer. This provides for the formation of interconnected pores. For example, the layers can be sequentially laid in incremental 60 degrees of rotation to produce a 0/60/120 layering pattern (such that the micro-filaments resemble an equilateral triangle when viewed in a plan view). Alternatively, the layers are sequentially laid in incremental 90 degrees of rotation. The layering pattern allows the formation of interconnected pores. The micro-filament mesh layers are adhered together to form the inner core structure.

In a further embodiment, the outer portion is rolled or wrapped around the inner portion. In one embodiment, the outer portion micro-filament mesh is the same porous bioresorbable polymer or polymer composite as used in the inner portion. The outer portion is joined to the inner portion, e.g., using heat fusion and hydrostatic pressure to form the scaffold implant. The thickness of the inner portion and the outer portion of the implant can be varied depending on the requirement of mechanical strength and cell proliferation rates. Furthermore, the size of the pores can adjusted be to control vascularization or new blood vessel growth and formation.

BRIEF DESCRIPTION OF THE DRAWINGS

The foregoing will be apparent from the following more particular description of example embodiments of the invention, as illustrated in the accompanying drawings. The drawings are not necessarily to scale, emphasis instead being placed upon illustrating embodiments of the present invention.

FIG. 6A is a photograph of a rabbit ulna after 16 weeks following implant of Group I (GP I: scaffold only).

FIG. 6B is a photograph of a rabbit ulna after 16 weeks following implant of Group II (GP II: scaffold+platelet rich plasma (PRP)).

FIG. 6C is a photograph of a rabbit ulna after 16 weeks following implant of Group III (GP III: scaffold+platelet rich plasma (PRP)+mesenchymal stem cells (MSC)).

DETAILED DESCRIPTION OF THE INVENTION

Figure 1A:
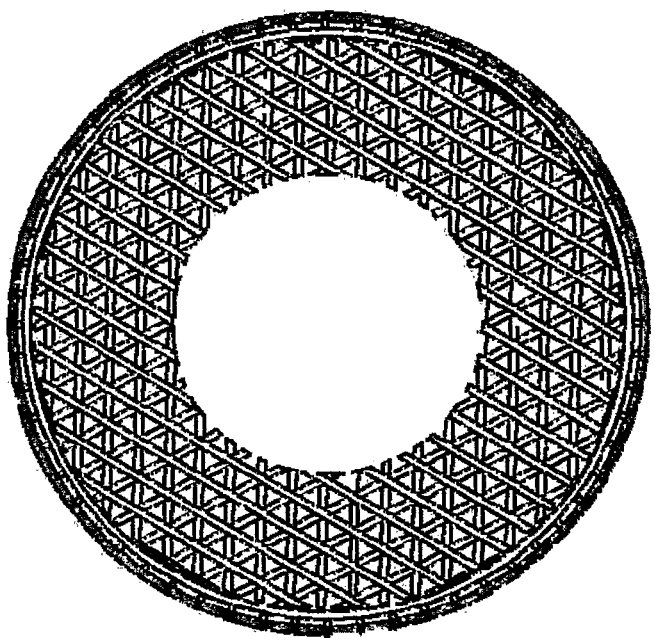
FIG. 1A is a drawing illustrating a close-up top view of a scaffold with a layered pattern, and showing the inner and outer portions of the scaffold.

The repair and reconstruction of large bone defects such as in the lengthening of the lower limb, has been a clinical challenge. Bone defects can occur as a result of congenital abnormalities, trauma or disease. This problem has yet to be solved. Presently none of the approaches proposed thus far have shown long term efficacy that resembles the natural bone. The era of tissue engineering involving stems cells and a suitable scaffold could provide the answer. However, a suitable scaffold has yet to be designed. Ceramics scaffolds such as macroporous hydroxyapaptite (HA) have been tried with some clinical success. But, ceramics are brittle material and the scaffolds are prone to premature fracture. Some, though bioactive, are not resorbable and pose long term infection risk. In many cases HA ceramics are crystalline in nature and hence do not render it resorbable even after 6 years.

Naturally-derived or synthetic materials can be fashioned into scaffolds that, when implanted in the body as temporary structures, provide a template that allows the body's own cells to grow and form new tissues while the scaffold is gradually absorbed. Conventional two-dimensional scaffolds are satisfactory for multiplying cells, but are less satisfactory when it comes to generating functional tissues. For that reason, a three-dimensional (3D) bioresorbable scaffold system is preferred for the generation and maintenance of highly differentiated tissues. Ideally, the scaffold should have the following characteristics: (i) be highly porous with an interconnected pore network for cell growth and flow transport of nutrients and metabolic waste; (ii) be biocompatible and bioresorbable, with controllable degradation and resorption rates so as to substantially match tissue replacement; (iii) have suitable surface chemistry for cell attachment, proliferation and differentiation; (iv) have enough channels to promote vascular integration and (v) have mechanical properties to match those of the tissues at the site of implantation. In vivo, the scaffold structure should protect the inside of the pore network proliferating cells and their extracellular matrix from being mechanically overloaded for a sufficient period of time (e.g., as would be desired for load-bearing tissues such as bone and cartilage). A biomechanically stable scaffold with mechano-induction properties is therefore sought after.

Bioresorbable polymeric scaffolds have been used but none have been designed for long bone tissue applications. Some of these polymers with high glass transition temperature, e.g., PGA (poly glycolic acid) and PLA (poly lactic acid), are also brittle and some degrade too fast, hence unable to evoke the long term mechano induction required for proper bone remodeling process. The large volume of acid formation, as a by product of degradation, of those with too short a degradation time, also hinders the proper cell formation and growth of the bone. The other issue is that large scaffolds of this nature do not have enough channels to provide the rich vasculature of blood vessels for drainage of waste products as well as delivery of nutrients over the entire volume.

Porosity and pore sizes play a critical role in bone formation in in vivo situations. Higher porosity and pore size has shown to result in greater bone ingrowth, however the mechanical properties are diminished in such instances. Present limitations thus set an upper function limit for pore size and porosity. Repair of bone tissue and rate of remodeling is thus compromised.

The present invention describes a method of fabrication and the design of a porous (having interconnected pores) scaffold that has a central channel and multiple side channels that is stiff but yet fracture resistant and with sufficient bending, compressive and torsional strength. The slow degradation of the scaffold allows for the 3D matrix to maintain structural integrity and mechanical properties during the remodeling process. Artificial or synthetic scaffolds as described herein are particularly useful in bone regeneration. For example, for use in orthopedic oral maxillofacial surgery to replace or repair a bone defect. In addition, the scaffolds described herein are ideal for long bone tissue engineering. For example, to augment the length of a bone in the upper and lower extremities of the human body.

The design which has a central channel to allow the packing or infusion of agents, such as cells, bone marrow, growth factors, drugs and combinations thereof. The circumference or outer portion of the scaffold is fabricated from a mesh of porous bioresorbable polymer or polymer composite. The outer portion is sufficiently porous to allow the communication of blood vessels (e.g., growth and expansion of blood vessels). The scaffold can be any suitable shape. In general, the suitable shape is any shape compatible for the particular bone structure being remodeled as will be appreciated by the skilled person, e.g., tubular, cylindrical, conical, truncated-cone, a pentahedron, a truncated-pentahedron, an elliptical or oval shaped column, or a combination thereof.

Bioresorbable polymers, both natural and synthetic, and which are biocompatible are well known in the art and include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. Suitable bioresorbable polymers can be chosen by the person skilled in the art using standard techniques and based on the mechanical and degradation properties of the polymer such that the polymer is chosen for its compatibility with bone remodeling. In one embodiment, the bioresorbable polymer or polymer composite comprises, consists, or consists essentially of polycaprolactone (PCL) or PCL-ceramic composite mesh.

In one embodiment, the scaffold is made from layers of micro-filament meshes, wherein the microfilaments are a bioresorbable polymer or polymer composite. The microfilaments in the meshes are in a parallel, or essentially parallel formation. Furthermore, the micro-filaments are spaced apart, such as at least, or about 200 microns to at least, or about 800 microns apart. By spacing the micro-filaments, the porosity of the scaffold can be controlled. For example, micro-filaments that are more widely spaced result in a scaffold with larger pores, and vice versa, micro-filaments that are closely spaced result in a scaffold with smaller pores. In one embodiment, the micro-filaments in the mesh are spaced at least, or about 200 microns, 250 microns, 300 microns, 350 microns, 400 microns, 450 microns, 500 microns, 550 microns, 600 microns, 650 microns, 700 microns, 750 microns, or 800 microns apart.

Each micro-filament mesh is laid in layers, one on top of the other, such that each layer is laid with the micro-filaments at a different angle from the previous layer. For example, the layers can be laid in incremental degrees ranging from about zero degrees to at least, or about 90 degrees. In one embodiment, the layers are sequentially laid in at least, or about 60 degrees of incremental rotation to produce a 0/60/120 layering pattern (such that the micro-filaments resemble an equilateral triangle when viewed in a plan view). Alternatively, the layers are sequentially laid in at least, or about 90 degrees of incremental rotation. The layering pattern allows the formation of interconnected pores. Other rotation patterns of layering can be used as will be recognized by persons skilled in the art to achieve suitable porosity characteristics.

The micro-filament mesh layers are adhered together to form the inner core structure. Any suitable means as known in the art using standard techniques can be used, e.g., sintering, or heat from the extruded fibers and cooling. In one embodiment, the layers of micro-filament meshes are adhered together by subjecting the layers of the scaffold to a hydrostatic pressure chamber (e.g., from at least, or about 0.01 atmosphere, 0.05 atmosphere, 0.1 atmosphere, 1 atmosphere, 2 atmosphere, 4 atmosphere, 6 atmosphere, 8 atmosphere, 10 atmospheres) at a temperature just below the melting point of the polymer (for example in the case of PCL it is at least, or about 55-60° C.) for a period of time (for example from at least, or about 30 to 45 min) to allow proper sintering of each layer.

The outer portion is rolled around, or wrapped around, the inner portion. In one embodiment, the outer portion is rolled around, or wrapped around, the circumference of the inner portion at least two or more times. In a particular embodiment, the outer portion is wrapped around the inner portion at least 2, 3, 4, or 5 times. In another embodiment, the outer portion micro-filament mesh is the same porous bioresorbable polymer or polymer composite as used in the inner portion. In another embodiment, the outer portion micro-filament mesh is different from the porous bioresorbable polymer or polymer composite as used in the inner portion. The outer portion is joined or adhered to the inner portion. For example, in one embodiment, the outer portion and inner portion of the scaffold are adhered together using heat fusion (e.g., at least, or about 90° C. to at least, or about 120° C.) and hydrostatic pressure to faun the scaffold implant.

The thickness of the inner portion and the outer portion of the implant can be varied depending on the requirement of mechanical strength and cell proliferation rates. For example, the inner portion of the scaffold can have a radial thickness of at least, or about 3 mm, to at least, or about 12 mm, or more and the outer portion of the scaffold can have a radial thickness of at least, or about 1.5 mm to at least, or about 2.5 mm, or more. In one embodiment, the inner portion of the scaffold has a radial thickness of at least, or about 3 mm, 4 mm, 5 mm, 6 mm, 7 mm, 8 mm, 9 mm, 10 mm, 11 mm, 12 mm, or more. In another embodiment, the outer portion of the scaffold has a radial thickness of at least, or about 1.5 mm, 1.6 mm, 1.7 mm, 1.8 mm, 1.9 mm, 2.0 mm, 2.1 mm, 2.2 mm, 2.3 mm, 2.4 mm, 2.5 mm, or more.

In one embodiment, the scaffold is sufficiently porous to allow, for example, seeding and growth of cells. For example, the size of the pores can adjusted be to control the rate of vascularization. In one embodiment, the pores are at least, or about 40 µm to at least, or about 300 µm in diameter. In a particular embodiment, the pore size is at least, or about 40 µm, 50 µm, 60 µm, 70 µm, 80 µm, 90 µm, 100 µm, 120 µm, 140 µm, 160 µm, 180 µm, 200 µm, 220 µm, 240 µm, 260 µm, 280 µm, or 300 µm. The porosity of the scaffold can be varied according to the needs. In one embodiment, the porosity of the scaffold is at least, or about 60% to at least, or about 80%. In a particular embodiment, the scaffold porosity is at least, or about, 60%, 65%, 70%, 75%, or 80%.

Additionally, the scaffold can be prepared with particular mechanical strengths. For example, in one embodiment, the scaffold has a compressive modulus value of at least, or about 200 MPa to at least, or about 500 MPa, or more. In a particular embodiment, the scaffold has a compressive modulus value of at least, or about 200 MPa, 250 MPa, 300 MPa, 350 MPa, 400 MPa, 450 MPa, 500 MPa, or more. In a particular embodiment, the outer portion of the scaffold has a compressive modulus value of at least, or about 200 MPa to at least, or about 500 MPa, or more. In one embodiment, the outer portion of the scaffold has a compressive modulus value of at least, or about 200 MPa, 250 MPa, 300 MPa, 350 MPa, 400 MPa, 450 MPa, 500 MPa, or more.

In another embodiment, the scaffold has a compressive strength of at least, or about 5.0 MPa to at least, or about 50 MPa, or more. In a particular embodiment, scaffold has a compressive strength of at least, or about 5.0 MPa, 10 MPa, 15 MPa, 20 MPa, 25 MPa, 30 MP, 35 MPa, 40 MP, 45 MPa, 50 MPa, or more. In another embodiment, the outer portion of the scaffold has a compressive strength of at least, or about 5.0 MPa to at least, or about 50 MPa, or more. In a particular embodiment, the outer portion of the scaffold has a compressive strength of at least, or about 5.0 MPa, 10 MPa, 15 MPa, 20 MP, 25 MPa, 30 MP, 35 MPA, 40 MP, 45 MPa, 50 MPa, or more.

In another embodiment, the scaffold has a torsional strength of at least, or about 40 Nm, to at least, or about 360 Nm, or more. In one embodiment, the scaffold has a torsional strength of at least, or about 40 Nm, 80 Nm, 120 Nm, 160 Nm, 200 Nm, 240 Nm, 280 Nm, 320 Nm, 360 Nm, or more. In a particular embodiment, the inner portion of the scaffold has a torsional strength of at least, or about 40 Nm, 80 Nm, 120 Nm, 160 Nm, 200 Nm, 240 Nm, 280 Nm, 320 Nm, 360 Nm, or more.

In a further embodiment, the scaffold has a bending strength of at least, or about 50 Nm to at least, or about 600 Nm, or more. In a particular embodiment, the inner portion of the scaffold has a bending strength of at least, or about 50 Nm, 100 Nm, 150 Nm, 200 Nm, 250 Nm, 300 Nm, 350 Nm, 400 Nm, 450 Nm, 500 Nm, 550 Nm, 600 Nm, or more.

The inner portion of the scaffold can further comprise a central channel having a diameter suitable for allow the packing or infusion of agents, such as cells, tissues, cell- or tissue-derived agents, growth factors, drugs and combinations thereof. The central channel has a diameter of any suitable size for the purposes being used. It can be determined from the bone remodeling or replacement procedure being used and will be specific to the individual patient needs, as determined by an appropriately skilled physician or technician. In one embodiment, the central channel has a diameter of at least, or about 5 mm to at least, or about 25 mm. In a particular embodiment, the central channel has a diameter at least, or about 5 mm, 10 mm, 15 mm, 20 mm, or 25 mm. The central channel can be filled, packed, infused, adsorbed with, and/or absorbed with, suitable agents. Such agents can be, e.g., a bioactive agent, or an inert agent, and combinations thereof. Inert agents can be any suitable agent, e.g., carrier, excipient, sterilizing solution, labeling solution, and the like.

Bioactive agents are also known in the art. For example, bone marrow, platelet-rich plasma, stem cells (e.g., mesenchymal stem cells), osteoblasts, osteoclasts, bone morphogenic proteins (BMP), vascular endothelial growth factors (VEGF), connective tissue growth factors (CTGF), osteoprotegerin, growth differentiation factors (GDFs), cartilage-derived morphogenic proteins (CDMPs), LIM mineralization proteins (LMPs), transforming growth factor beta (TGFβ), antibiotics, immunosuppressive agents, and combinations thereof.

Examples of bone morphogenic proteins (BMP) include: BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; and BMP-18. Vascular endothelial growth factors (VEGF) include VEGF-A, VEGF-B, VEGF-C, VEGF-D and VEGF-E. Connective tissue growth factors (CTGF) include CTGF-1, CTGF-2, and CTGF-4. Growth differentiation factors (GDFs) include GDF-1, GDF-2, GDF-3, GDF-7, GDF-10, GDF-11, and GDF-15. Cartilage-derived morphogenic proteins (CDMPs) include CDMP-1 and CDMP-2. LIM mineralization proteins (LMPs) include LMP-1, LMP-2, and LMP-3. Transforming growth factor beta (TGFβ) include TGFβ-1, TGFβ-2, and TGFβ-3.

Examples of antibiotics useful with the biocompatible composite material include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamethoxazole, and vancomycin.

Suitable immunosuppressive agents that can be included in the biocompatible composite material, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3) Sandimmune™, Neora.™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

Additional, or alternative non-limiting examples of agents include collagen, drugs, antibodies, peptides, peptidomimetics, oligonucleotides, chemical entities, growth factors, and mixtures thereof.

As will be appreciated by those in the art, bioactive agents can be polypeptides, including full length polypeptides, biologically active fragments thereof, and fusion proteins, small molecules, and cells expressing such bioactive agents. Furthermore, the concentrations of the bioactive agent can be variable based on the desired length or degree of activity required. In one embodiment, the central channel is filled, packed, infused, adsorbed with, and/or absorbed with a combination of platelet-rich plasma and mesenchymal stem cells.

The scaffold can further comprise side channels (also referred to herein as micro through-holes) in the scaffold. Such side channels allow the communication of blood vessels, for example. The side channels can be randomly or uniformly spaced. In one embodiment, the side channels are uniformly spaced. Spacing can be any spacing suitable to meet the needs of the scaffold. For example, the side channels are spaced at least, or about 250 microns to at least, or about 700 microns apart, or more. In one embodiment, the side channels are spaced at least, or about 250 microns, 300 microns, 350 microns, 400 microns, 450 microns, 500 microns, 550 microns, 600 microns, 650 microns, 700 microns, or more apart. The diameter of the side channels can vary. In one embodiment, the diameter of the side channels are at least, or about 50 microns to at least, or about 700 microns. In a particular embodiment, the diameter of the side channels are at least, or about 50 microns, 100 microns, 150 microns, 200 microns, 250 microns, 300 microns, 350 microns, 400 microns, 450 microns, 500 microns, 550 microns, 600 microns, 650 microns, or 700 microns.

As will be appreciated by the skilled artisan, the scaffold generally has two ends. The ends can be open-ended, closed ended, or open-ended at one end and closed ended at the other end. One or both ends of the scaffold can be closed by addition of one or more layers of micro-filament mesh. The micro-filament can be the same or different as the micro-filament mesh of the inner and/or outer portion of the scaffold.

The scaffolds described herein are particularly useful in bone regeneration to repair or replace a bone defect, e.g., in orthopedic oral maxillofacial surgery. In addition, the scaffolds described herein are ideal for long bone tissue engineering. For example, to augment the length of a bone in the upper and lower extremities of the human body. In one embodiment, a scaffold as described herein is implanted into a patient in need of bone regeneration or long bone tissue engineering. The scaffold can be implanted with or without additional bioactive and/or inert agents. Furthermore, the scaffolds can be cultured in vitro with cells isolated from a donor, such as a patient, before implanting the scaffold into a patient. Such "pre-culturing" of the scaffold initiates mineralization of the implant and promotes cellular proliferation and integration of the scaffold when implanted into the patient.

Exemplification

Figure 1B:
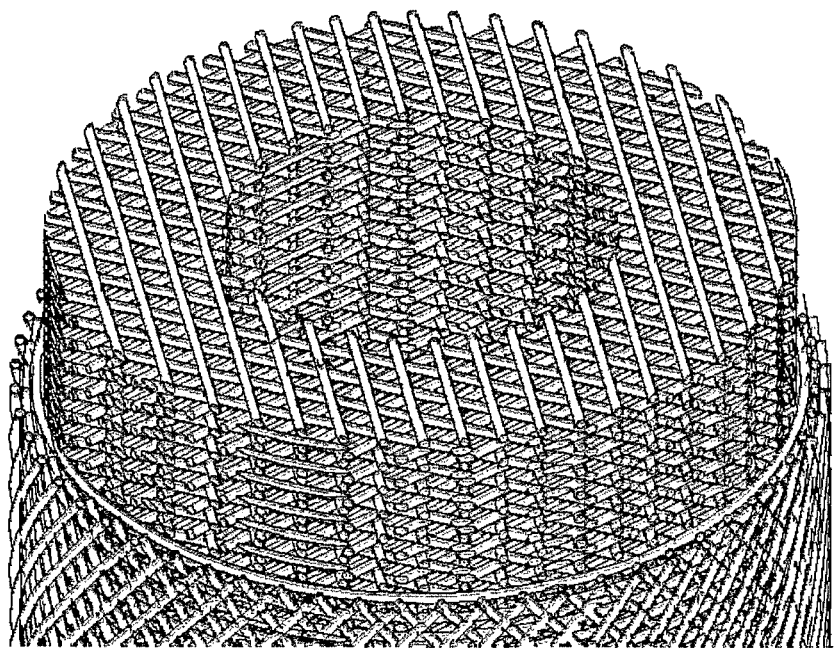
FIG. 1B is a drawing illustrating a close-up isometric view of a scaffold with a layered pattern, and showing the inner and outer portions of the scaffold.
Figure 2:
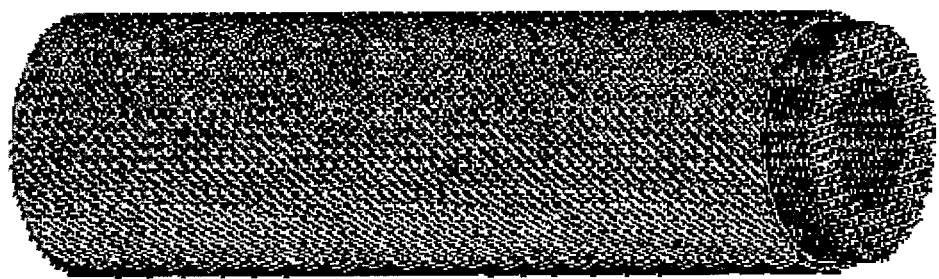
FIG. 2 is a drawing illustrating an isometric side view of a scaffold with a layered pattern, and showing the inner and outer portions of the scaffold.
Figure 3:
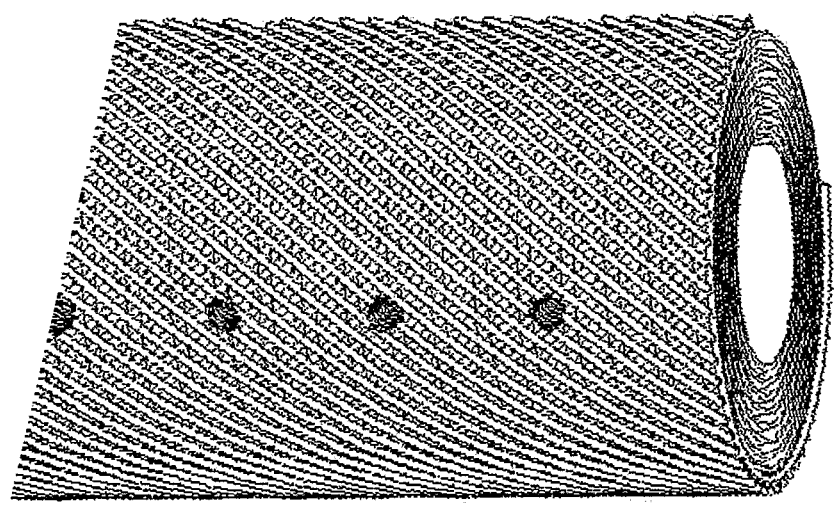
FIG. 3 is a drawing illustrating an isometric side view of a scaffold with a layered pattern and smaller side channels (also referred to herein as micro through-holes).
Figure 4A:
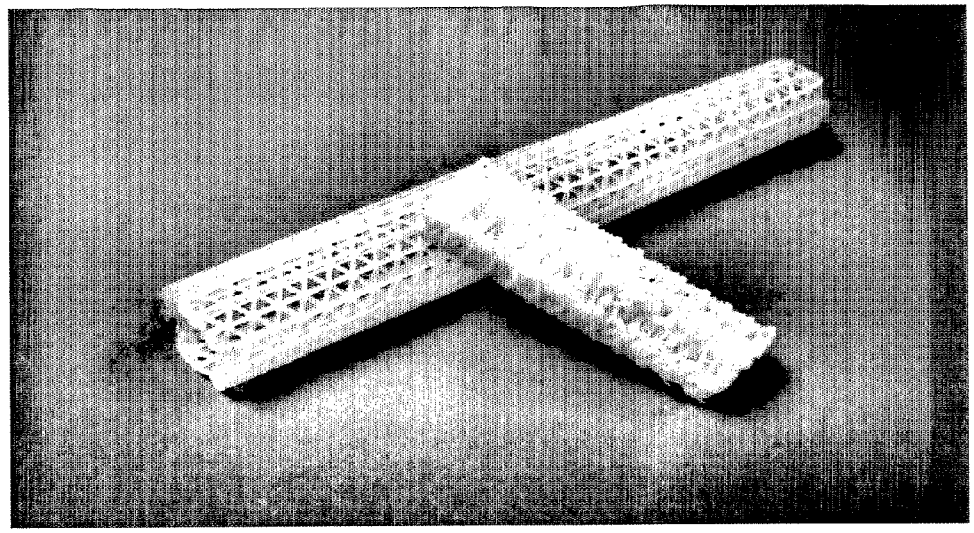
FIG. 4A is a photograph depicting the inner portion and outer portion of the scaffold before joining together. The outer portion is secured or joined to the inner portion using standard techniques, e.g., sintering, heat fusion with hydrostatic pressure.
Figure 4B:
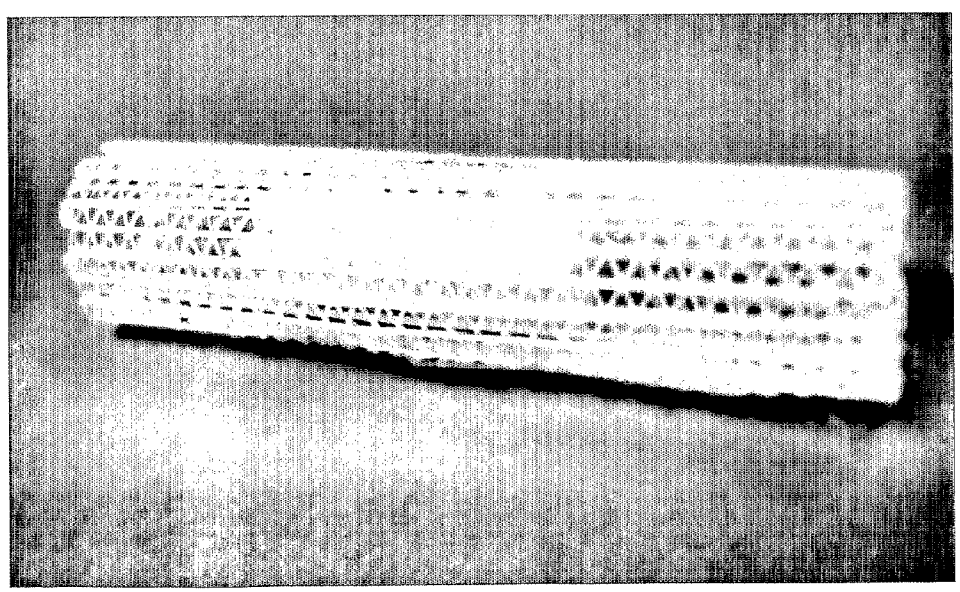
FIG. 4B is a photograph depicting the inner portion and outer portion of the scaffold after joining together to form the scaffold.
Figure 5A:
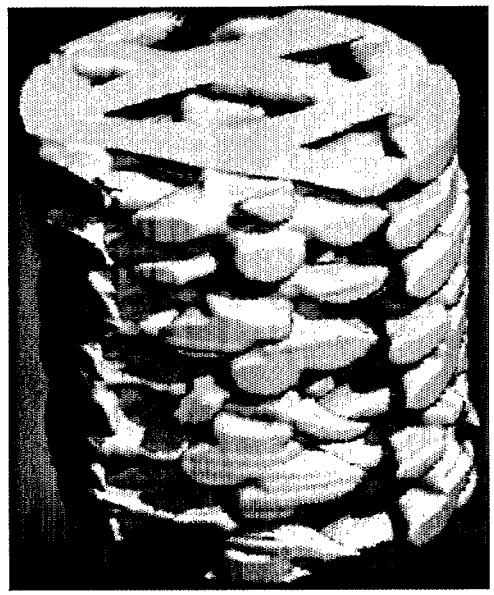
FIG. 5A is a micro-CT image of an isometric view of the internal structure of a PCL-TCP 3D scaffold.
Figure 5B:
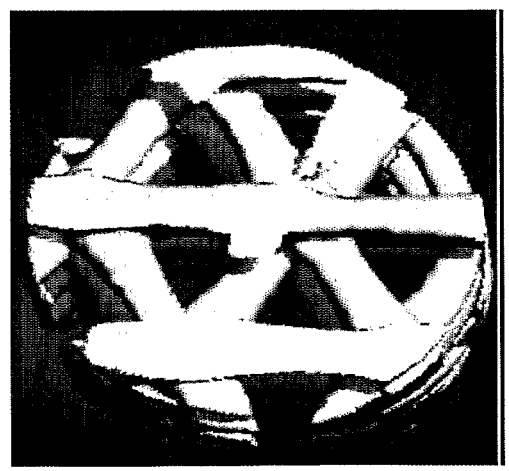
FIG. 5B is a micro-CT image of a top view demonstrating through porosity of the internal structure of a PCL-TCP 3D scaffold.

Bone Regeneration Using PCL-TCP Scaffolds with Human Bone MSC and PRP in Rabbit Ulna Scaffold Preparation Polycaprolactone-tricalcium phosphate (PCL-TCP) (80:20%) composite scaffolds, manufactured by Osteopore International Pte Ltd, Singapore (for example, as illustrated in FIGS. 1A, 1B and FIG. 2), were sterilized by ethylene oxide gas at low temperature (below 40° C.) (Osteopore International). As will be appreciated by the skilled artisan, scaffolds can be sterilized in any suitable manner using standard techniques including treatment with alcohol. Scaffolds were prepared by fused deposition modeling extrusion. In one example, the scaffolds have a height of approximately 10 mm and a diameter of approximately 4 mm having a layering pattern of 0/60/120 degrees (see FIGS. 5A and 5B where the outer sleeve was removed to show the micro architecture). The size of the pores is this particular example 500 µm. The modulus strength of these scaffolds may be between 5-50 MPa and preferably as in this example around 23 MPa, the compressive strength of these scaffolds may be between 4-10 MPa and preferably an in this example around 6.38 MPa Preparation of Platelet-Rich Plasma Platelet-rich plasma was prepared from whole blood samples from rabbits. Arterial blood was collected from the aorta of New Zealand white rabbit (male, 6-weeks of age) under anesthesia. 50 ml of blood was first centrifuged at 2000 rpm for 3 min at room temperature to separate both the platelet rich plasma (PRP) and platelet poor plasma (PPP) portions from the red blood cell fraction. Then, the PRP and PPP portions were again centrifuged at 5000 rpm for 5 min to separate the PRP (5 ml).

Culture of Human Cord Blood Mesenchymal Stem Cells

Human cord blood mesenchymal stem cells (MSC) were purchased from Medipost Co., Ltd. and cultured in alpha Modified Eagle's Medium (α-MEM, GIBCO BRL) supplemented with 20% fetal bovine serum (FBS, GIBCO BRL) and antibiotic-antimycotic (GIBCO BRL). Medium was changed three times per week and cultured for three passages (P3) until confluence (~7 days).

Animals

15 New Zealand White rabbits, 6 weeks old were used. The rabbits were anesthetized with zoletile 50 (0.2 ml/kg, Virvac Korea). Under sterile conditions, the ulna was exposed and a 10 mm segmental critical size defect $CaCl_2$ was made using a cutting saw. Scaffold was then implanted into the ulna and closure of wound was performed. Three groups were designed: Group 1-PCL-TCP scaffold only; Group 2-PCL-TCP scaffold with PRP; and Group 3-PCL-TCP scaffold with PRP and MSC.

PRP/PCL-TCP scaffold were prepared by mixing of PRP 300 ul and thrombin-$CaCl_2$ mixture solution 50 ml. The thrombin-$CaCl_2$ mixed scaffolds were seeded by direct mixing and loading with $3 \times 10^6$ human cord blood mesenchymal stem cells.

Evaluation

Evaluation methods were as follows.

2D Radiography:

Antero-Posterior (AP) and lateral radiographs using X-Ray analysis were performed at time points 4 weeks, 8 weeks, 12 weeks and 16 weeks.

3D Micro CT Evaluation:

Skyscan 1072, voltage 80 kVP and current of 100 µA. Trabecular thickness, trabecular separation and BVF (bone volume fraction) were calculated at 12 week and 16 week time points.

Bone Mineral Density (BMD) Evaluation:

Lunar PIXImus Using a scanning machine, regions of interest of the tissue specimen taken at 12 week and 16 week time points were divided into squares of 0.08 cm² area.

Histological Evaluation:

At 12 week and 16 week time points: 1. Thin sections were cut from paraffin embedded tissue. 2. Histological sections were stained with hematoxylin (Sigma Aldrich Harris Hematoxylin Modified, HHS128-4L) and Eosin (Sigma Aldrich Eosin Y solution, HT1102128-4L) using standard procedures. 3. Deparaffination of paraffin embedded tissue was accomplished by treatment with xylene for 5 minutes for 3 times, followed by dehydration in graded alcohols (100%, 95%, 90%, 80%, 70%) 3 times each and rinsed in water for 1 minute.

Results

Gross Examination

All rabbits healed uneventfully. Gross examination (FIG. 7) of explanted scaffolds revealed that the scaffolds were fully integrated into the surrounding host tissue and the ulna region was recontoured.

Figure 7:
FIG. 7 is an X-ray of the lateral view of the ulna after 12 weeks following implantation of each GP I, GP II, or GP III scaffolds. Complete union of the bone with the scaffolds is demonstrated for each scaffold tested.

2D radiography (X-Ray analysis) showed that all specimens had complete union by week 12 (see FIG. 7). An average of amount of new bone formation in each group is shown in Table 1 below:

TABLE 1

Bone formation in each group

| Time | Gp I: Scaffold only | Gp II: Scaffold + PRP | Gp III: Scaffold + PRP + MSC |
|---|---|---|---|
| 4 weeks | 50% | 46.60% | 80% |
| 8 weeks | 75% | 75% | 100% |
| 12 weeks | 100% | 100% | 100% |
| 16 weeks | 100% | 100% | 100% |

3D Micro CT Evaluation

The trabecular thickness (see Table 2) and trabecular separation (see Table 3) were calculated. Group III is slightly thicker and a less separated trabecular pattern as compared to Group I; but generally within statistical accuracy, it can be seen from the two tables the results are indicative of a well developed trabecular bone structures in all three groups.

TABLE 2

Trabecular Thickness Distribution at 16 wks

| Trabecular Thickness | Gp I (%) | Gp II (%) | Gp III (%) |
|---|---|---|---|
| >0.000 mm-0.043 mm | 6.9 | 4.8 | 1.5 |
| >0.043 mm-0.085 mm | 8.2 | 5.8 | 2.8 |
| >0.085 mm-0.171 mm | 15.9 | 13 | 7.1 |
| >0.171 mm-0.341 mm | 37.3 | 37.8 | 25.4 |
| >0.341 mm-0.682 mm | 31 | 38.7 | 53.9 |
| >0.682 mm-1.364 mm | 0.6 | 0 | 9.3 |
| >1.364 mm-2.729 mm | 0 | 0 | 0 |
| >2.729 mm-5.458 mm | 0 | 0 | 0 |

TABLE 3

Trabecular Separation Distribution at 16 wks

| Trabecular Separation | Gp I (%) | Gp II (%) | Gp III (%) |
|---|---|---|---|
| >0.000 mm-0.043 mm | 1.5 | 1.6 | 3.9 |
| >0.043 mm-0.085 mm | 2.4 | 2.7 | 6.2 |
| >0.085 mm-0.171 mm | 6.4 | 8.2 | 12.8 |
| >0.171 mm-0.341 mm | 21.9 | 23.4 | 28.1 |
| >0.341 mm-0.682 mm | 41.7 | 49.2 | 47.1 |
| >0.682 mm-1.364 mm | 26.1 | 15 | 1.8 |
| >1.364 mm-2.729 mm | 0 | 0 | 0 |
| >2.729 mm-5.458 mm | 0 | 0 | 0 |

Bone Volume Fraction

Figure 8:
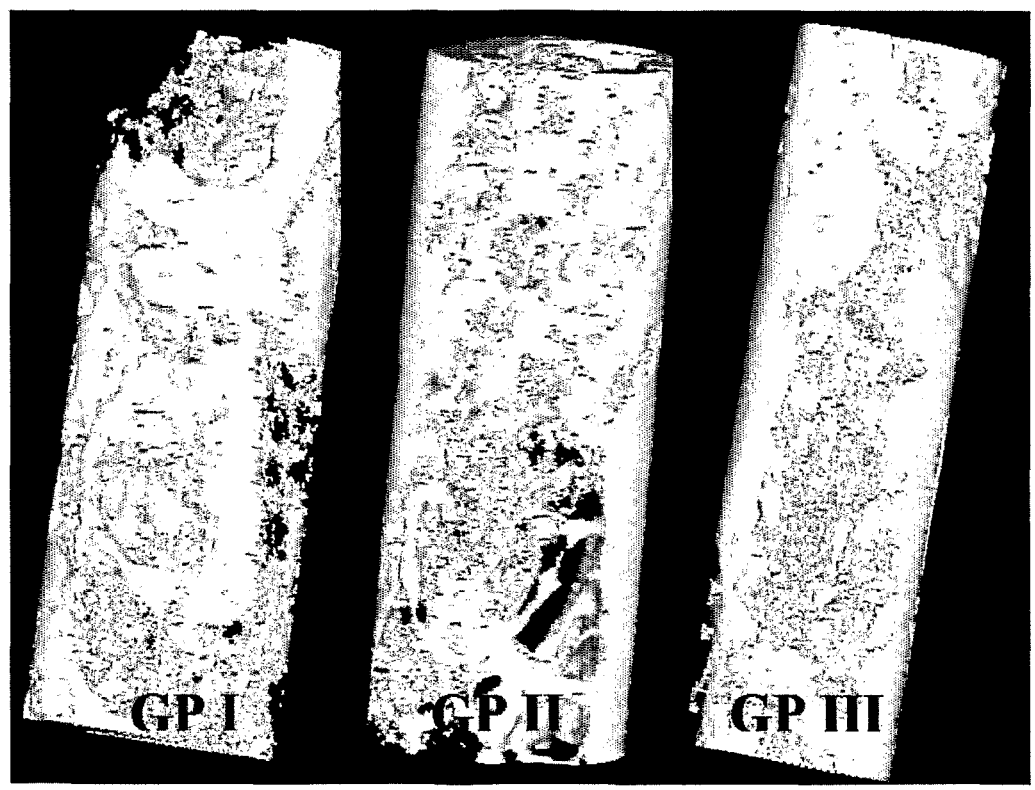
FIG. 8 is a micro-CT image of bone formation after 16 weeks following implantation of each GP I, GP II, or GP III scaffolds.

FIG. 8 shows a typical micro-CT images of bone formation for the three groups at week 16. Complete union can be seen in all groups. GP III appears to give the best results in terms of bone quality.

Figure 9:
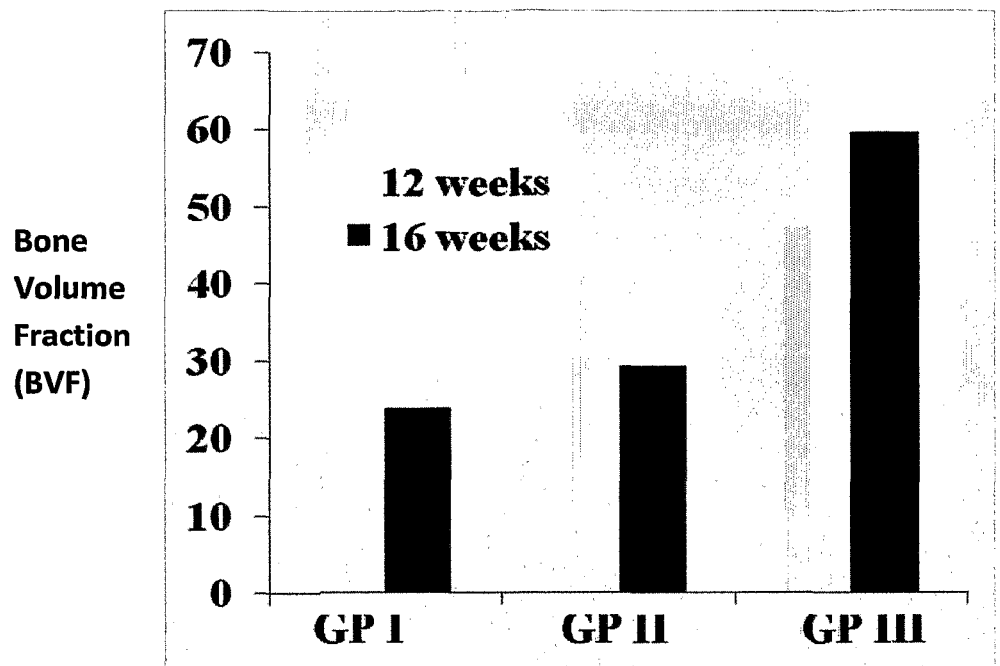
FIG. 9 is a graph charting a quantitative comparison of bone volume fraction of GP I, GP II, and GP III scaffolds at 12 weeks and 16 weeks as determined by micro-CT analysis.

Bone volume fraction was defined as area of new bone formation divided by area of total bone defect. Group III demonstrates better new bone formation as compared to the two groups with in increase from week 12 to Week 16 while the other 2 groups showed a slight decline (Table 4 and FIG. 9).

TABLE 4

Average of bone volume fraction of each group

| Time | Group I | Group II | Group III |
|---|---|---|---|
| 12 weeks | 36% | 30% | 47% |
| 16 weeks | 24% | 29% | 59% |

Bone Mineral Density Evaluation

Figure 10:
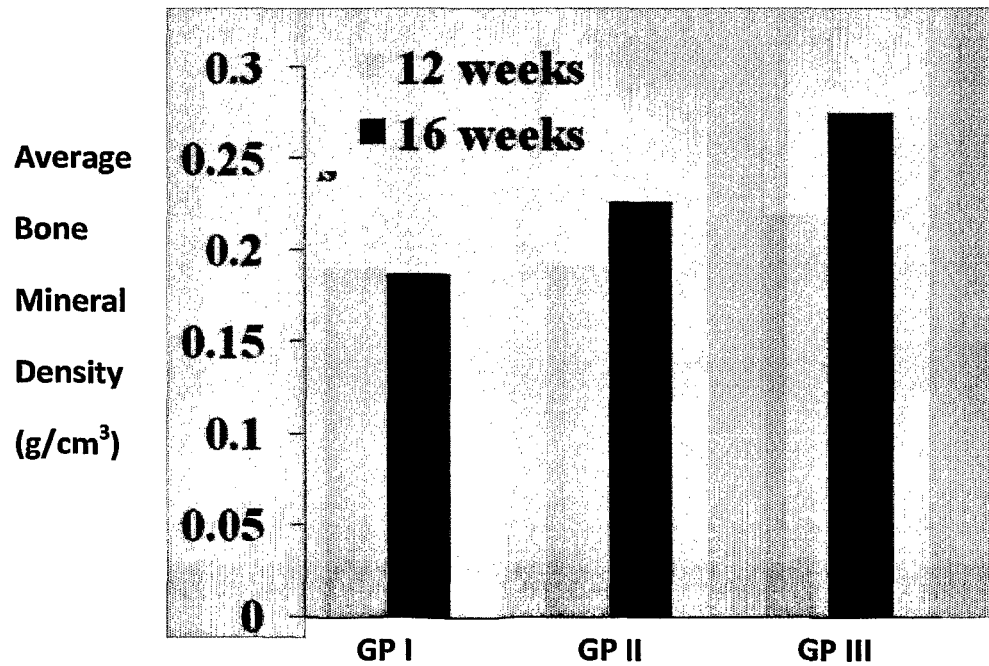
FIG. 10 is a graph charting bone mineral density of GP I, GP II, and GP III scaffolds samples at 12 weeks and 16 weeks as determined by PIXImus densitometer.

The average bone mineral density is shown in Table 5 for each group. At week 12, Group I exhibited a lower value when compared to Group II and Group III. However at week 16, Group III gave the best results. This is seen more clearly in FIG. 10.

TABLE 5 average of bone mineral density of each group (g/cm³)

| Time | Gp I | Gp II | Gp III |
|---|---|---|---|
| 12 weeks | 0.19 | 0.19 | 0.22 |
| 16 weeks | 0.18 | 0.22 | 0.27 |

Histological Evaluation

Figure 11:
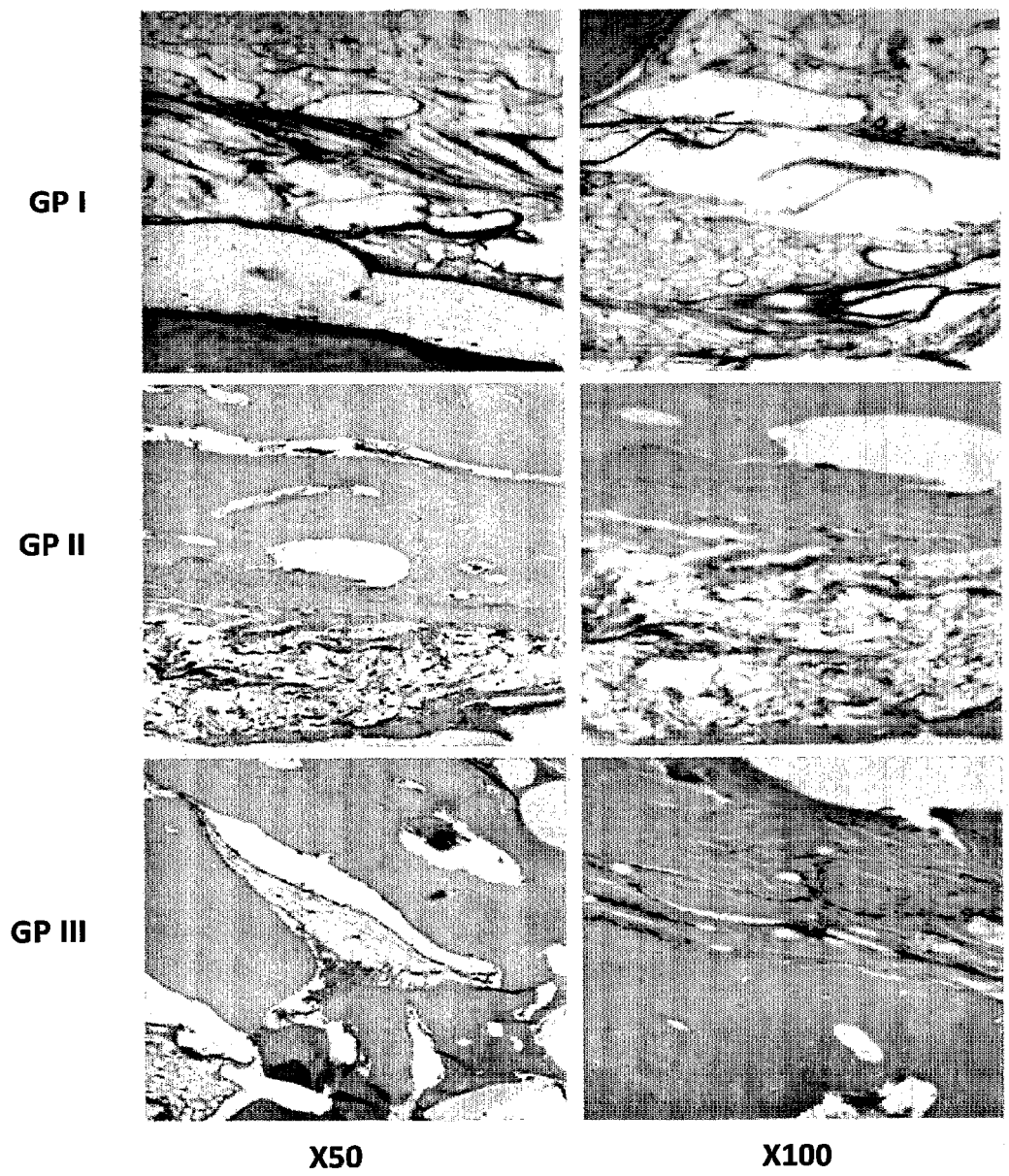
FIG. 11 is a series of hematoxylin and eosin (H&E) stained GP I, GP II, and GP III scaffolds samples at 16 weeks after implantation. Shown are H&E stained samples at ×50 (left) and ×100 (right) magnifications.

At 12 and 16 weeks, H&E staining of the bone specimen in groups were evaluated. In all groups, we observed an abundance of new osteoid tissue inside the scaffold at 12 and 16 weeks. New bone formation was more evident in the MSC/PRP/PCL-TCP scaffolds (GP III) (FIG. 11).

CONCLUSIONS

Bone regeneration using the scaffold implant with and without human cord blood MSC (Mesenchymal Stem Cells) and PRP (Platelet Rich Plasma) was demonstrated in a rabbit ulna segmental defect model. In this study, a 10 mm critical sized defect was created in a rabbit ulna and the scaffold implant was then implanted. Histological evaluation, Micro CT evaluation, Bone Mineral Density evaluation was performed. The results of this 3 month study has demonstrated new bone formation in the rabbit ulna defect model. The implant was fully integrated into the surrounding host tissue and the ulna region was recontoured demonstrating good biocompatibility. The scaffolds were also compatible with PRP and MSC. The incorporation of MSC seems to give the best results. The scaffolds all fused, formed new bone and were also strong enough to provide sufficient mechanical strength for the rabbit. The scaffold is ideal for long bone tissue engineering.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A bioresorbable scaffold for long bone tissue engineering comprising an inner portion and an outer portion surrounding the inner portion, wherein:
   a) the inner portion comprises a porous microfilament polymer having interconnected pores, wherein the inner portion is formed from layers of microfilament meshes joined together, each microfilament mesh having microfilament polymer threads in a series of spaced, parallel lines, and wherein each layer of microfilament mesh is positioned on the previous layer at an angle of about 60 degrees relative to the microfilament polymer threads in the previous layer, thereby producing an inner portion comprising a porous microfilament polymer having interconnected pores, and
   b) the outer portion comprises a bioresorbable microfilament mesh.

2. The bioresorbable scaffold of claim 1, wherein the inner portion further comprises a central channel.

3. The bioresorbable scaffold of claim 2, wherein the central channel further comprises a bioactive agent, an inert agent, or a combination thereof.

4. The bioresorbable scaffold of claim 3, wherein the bioactive agent is bone marrow, platelet-rich plasma, mesenchymal stem cells, osteoblasts, osteoclasts, a bone morphogenic protein (BMP), a vascular endothelial growth factor (VEGF), a connective tissue growth factor (CTGF), osteoprotegerin, a growth differentiation factor (GDFs), a cartilage-derived morphogenic protein (CDMPs), a LIM mineralization protein (LMPs), transforming growth factor beta (TGFβ), an antibiotic, an immunosuppressive agent, or a combination thereof.

5. The bioresorbable scaffold of claim 1, wherein the inner portion, the outer portion, or both the inner portion and outer portion of the scaffold comprises polycaprolactone (PCL) or a PCL-ceramic composite mesh.

6. The bioresorbable scaffold of claim 1, wherein the scaffold has a compressive strength of from about 5.0 MPa to about 50 MPa.

7. The bioresorbable scaffold of claim 1, wherein the scaffold has a compressive modulus of from about 200 MPa to about 500 MPa.

8. The bioresorbable scaffold of claim 1, wherein the scaffold has a porosity of from about 60% to about 80%.

9. The bioresorbable scaffold of claim 1, wherein the outer portion of the scaffold has a radial thickness of from about 1.5 mm to about 2 mm, and the inner portion of the scaffold has a radial thickness of from about 5 mm to about 10 mm.

10. The bioresorbable scaffold of claim 1, wherein the layers of microfilament meshes of the inner layer and the bioresorbable microfilament mesh of the outer layer are fused together.

11. The bioresorbable scaffold of claim 1, wherein the scaffold further comprises side channels through the inner and outer portions of the scaffold.

12. A method of preparing the bioresorbable scaffold of claim 1, comprising:
   a) layering bioresorbable microfilament meshes in sequential layers, wherein each microfilament mesh comprises microfilament threads lined in a spaced, parallel arrangement, and wherein each layer is positioned onto the previous layer at an angle of at least, or about 60 degrees relative to the microfilament threads in the previous layer;
   b) joining the layered microfilament meshes thereby forming a scaffold inner portion; and
   c) joining an outer layer of bioresorbable microfilament mesh around the inner portion, thereby producing a bioresorbable scaffold.

13. The method of claim 12, wherein the bioresorbable microfilament mesh of the scaffold inner portion and outer layer are each independently selected from polycaprolactone (PCL), PCL-ceramic, and a combination thereof.

14. The method of claim 12, wherein the layered microfilament meshes are joined together by sintering.

15. The method of claim 12, wherein the inner portion and outer layer are joined together by sintering.

16. The method of claim 12, wherein the scaffold has a compressive strength from about 5 MPa to about 50 MPa, and a compressive modulus of about 200 MPa to about 500 MPa.

17. The method of claim 12, wherein the scaffold has a porosity of from about 60% to about 80%.

18. The method of claim 12, wherein the scaffold further comprises side channels through the inner and outer portions of the scaffold.

19. The method of claim 12, wherein the diameter of the side channels is from about 50 microns to about 700 microns.

20. A bioresorbable scaffold for long bone tissue engineering comprising an inner portion and an outer portion surrounding the inner portion, wherein:
   a) the inner portion comprises a porous microfilament polymer having interconnected pores, wherein the inner portion is formed from substantially planar layers of microfilament meshes joined together, each microfilament mesh being substantially the same size and having microfilament polymer threads in a series of spaced, parallel lines, and wherein each layer of microfilament mesh is positioned on the previous layer at an angle of about 60 degrees relative to the microfilament polymer threads in the previous layer, thereby producing an inner portion comprising a porous microfilament polymer having interconnected pores, and defining a primary axis, the primary axis being substantially perpendicular to the substantially planar layers of the microfilament meshes, the inner portion further comprising a central channel substantially parallel to the primary axis, and
   b) the outer portion comprises a bioresorbable microfilament mesh substantially parallel to the primary axis.

* * * * *

UNITED STATES PATENT AND TRADEMARK OFFICE
CERTIFICATE OF CORRECTION

PATENT NO. : 8,702,808 B2  Page 1 of 1
APPLICATION NO. : 13/124161
DATED : April 22, 2014
INVENTOR(S) : Teoh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 258 days.

Signed and Sealed this

Twenty-ninth Day of September, 2015

Michelle K. Lee
*Director of the United States Patent and Trademark Office*